United States Patent [19]

McCain et al.

[11] Patent Number: 4,737,544

[45] Date of Patent: Apr. 12, 1988

[54] BIOSPECIFIC POLYMERS

[75] Inventors: G. Howard McCain; Robert D. Jarrett, both of Painesville, Ohio

[73] Assignee: BioSpecific Technologies, Inc., Painesville, Ohio

[21] Appl. No.: 86,307

[22] Filed: Aug. 14, 1987

Related U.S. Application Data

[63] Continuation-in-part of Ser. No. 515,949, Jul. 20, 1983, Pat. No. 4,687,808, which is a continuation-in-part of Ser. No. 407,613, Aug. 12, 1982, abandoned, and a continuation-in-part of Ser. No. 407,614, Aug. 12, 1982, abandoned.

[51] Int. Cl.$^4$ .................................... C07D 251/02
[52] U.S. Cl. ............................ 525/54.1; 604/4; 604/5; 604/6; 424/78; 424/409; 424/422; 427/2
[58] Field of Search ............... 604/4, 5, 6; 424/409, 424/422, 78; 427/2; 525/54.1

[56] References Cited

U.S. PATENT DOCUMENTS

| | | | |
|---|---|---|---|
| Re. 31,712 | 10/1984 | Giese | 428/407 |
| 3,787,380 | 12/1974 | Stamberger | 526/260 |
| 3,826,678 | 7/1974 | Hoffman et al. | 604/5 |
| 4,059,685 | 11/1977 | Johnson | 525/54.1 |
| 4,061,141 | 12/1977 | Hyden et al. | 128/214 R |
| 4,070,348 | 12/1978 | Kraemer et al. | 516/261 |
| 4,182,750 | 1/1980 | Sullivan et al. | 604/5 |
| 4,192,748 | 3/1980 | Hyden | 210/87 |
| 4,222,907 | 7/1980 | Katz | 524/17 |
| 4,239,743 | 12/1980 | Sedlacek et al. | 424/1 |
| 4,272,549 | 6/1981 | Carazza | 424/316 |
| 4,292,296 | 9/1981 | Parsons, Jr. | 424/1 |
| 4,305,926 | 12/1981 | Everse et al. | 424/54 |
| 4,357,311 | 11/1982 | Schutt | 525/54.1 |
| 4,362,155 | 12/1982 | Skurkovitch | 604/6 |
| 4,381,004 | 4/1983 | Babb | 128/214 R |
| 4,430,229 | 2/1984 | Yamawaki et al. | 210/692 |
| 4,614,513 | 9/1986 | Bensinger | 604/6 |
| 4,656,308 | 4/1987 | Schirmann | 560/170 |

FOREIGN PATENT DOCUMENTS

| | | |
|---|---|---|
| 1104110 | 6/1981 | Canada . |
| 0028937 | 5/1981 | European Pat. Off. . |
| 0054249 | 6/1982 | European Pat. Off. . |
| 0054799 | 6/1982 | European Pat. Off. . |
| 0082345 | 6/1983 | European Pat. Off. . |
| 0107509 | 5/1984 | European Pat. Off. . |
| 3109123 | 9/1982 | Fed. Rep. of Germany . |
| WO84/0774 | 3/1984 | PCT Int'l Appl. . |
| 1429534 | 3/1976 | United Kingdom . |
| 2092470 | 8/1982 | United Kingdom . |

OTHER PUBLICATIONS

Malchesky et al, "On-Line Separation of Macromolecules by Membrane Filtration with Cryogelation," *Artif. Organs*, 4:205 (1980).

Terman et al, "Specific Removal of Bovine Serum Albumin (BSA) Antibodies in vivo by Extracorporeal Circulation over BSA Immobilized on Nylon Microcapsules", *J. of Immunology*, vol. 116, No. 5, pp. 1337–1341 (1976).

Terman et al, "Specific Extraction of Antigen in vivo by Extracorporeal Circulation over Antibody Immobilized in Collodion-Chemical,"*J. of Immun.*, vol. 117, No. 5, pp. 1971–1975 (1976).

Terman et al., "Extracorporeal Immunoadsorption: Initial Experience in Human Systemic Lupus Erythematosus", *The Lancet*, Oct. 20, 1979, pp. 824–826.

Terman et al, "Specific Removal of Circulated Antigen by Means of Immuneadsorption,"*FEBS Letters*, vol. 61, No. 1, Jan. 1976, pp. 59–62.

Bansal et al, "Ex vivo Removal of Serum IgG in a Patient with Colon Certcinoma," *Cancer* 42(1), pp. 1–18 (1978).

(List continued on next page.)

*Primary Examiner*—Delbert R. Phillips
*Assistant Examiner*—Nathan M. Nutter
*Attorney, Agent, or Firm*—Thoburn T. Dunlap

[57] ABSTRACT

Biocompatible polymers having immobilized biologicals which retain a high specificity for binding pathological effectors, specific groups of pathological effectors or specific body fluid components are disclosed.

16 Claims, 2 Drawing Sheets

OTHER PUBLICATIONS

Terman et al, "Removal of Circulating Antigen and Immune Complexes with Immunoreactive Collodion Membranes", *FEBS Letters*, vol. 68, No. 1 (1976).

Ratner et al, "Synthetic Hydrogels for Biomedical Applications," ASC Symp. Ser. 1976, vol. 31, pp. 1-36.

A. S. Hoffman, "Use of Radiation Technology in Preparing Materials for Bioengineering and Medical Science," Ind. Appl. Radiosat. Radiat. Technol. Proc, Int. Conf., 1982 pp. 279-321.

Hoffman et al, "New Approaches to Non-Thrombogenic Materials," *Coagulation*: Curv. Res. Clim. Appl., Proc. Symp., 1972, pp. 201-226.

Jeffrey McCullough, M.D., "Therapeutic Plasma Exchange", Laboratory Medicine, vol. 12 (12). pp. 745-753, (1981).

American Cyanamid Compnay Product Bulletin MAGME Multifunctional Acrylic Monomer (p. 18).

MAGME/HEMA/MMA
(30/20/50)

GMA/NVP/HEMA
(50/46/4)

POLYCARBONATE
SUBSTRATE

BIOSPECIFIC POLYMERS

CROSS-REFERENCE TO RELATED APPLICATIONS

This application is a continuation-in-part of application Ser. No. 515,949, filed July 20, 1983, now U.S. Pat. No. 4,687,808, which is a continuation-in-part of application Ser. Nos. 407,613 and 407,614, filed on Aug. 12, 1982, both now abandoned.

BACKGROUND OF THE INVENTION

The course of many disease states is often reflected by elevated levels of specific blood proteins and other molecules. This phenomenon is typically utilized as a diagnostic tool to define the pathology and to follow the course of clinical treatment. In many instances, these specific blood proteins are directly or indirectly responsible for the primary and secondary manifestations of the disease process. "Autoimmune" diseases can be described as diseases characterized by circulating antibodies to endogenous substrates and tissue proteins required by the body for normal growth and maintenance. "Neoplastic" diseases are typically characterized by uncontrolled growth of an undifferentiated transformed cell line which evades or compromises the body's natural defense mechanisms by producing immunosupressive blocking factors, surface antigen masking components and/or growth regulator constituents. Specific compartmentalization of these pathological effectors (e.g., causitive agent) onto a biocompatible substrate is consistent with the restoration of "normal" body function by removal of the pathological effectors of the disease process.

The basic function of the organs, cells and molecules that comprise the immune system is to recognize and to eliminate from the body foreign substances. These foreign substances are eliminated by reaction between the foreign substance and antibodies which are formed in response to the substance. In general, this function is performed efficiently and without detriment to the host. However, in certain instances, disturbances can occur which can lead to pathogenic disorders such as, for example, an uncontrolled response (allergic disorders) or an abnormal response (autoimmune disease). The pathogenesis of both of these disorders is related directly or indirectly to the production of antibodies with cross reactivities to either environmental antigens (allergens) or self-antigens.

An autoimmune disease is a pathological condition arising when a host responds immunologically by production of antibodies with reactivity to a self-antigen. Autoimmunity can affect almost every part of the body, and generally involves a reaction between a self-antigen and an immunoglobulin (IgM or IgG) antibody. Representative autoimmune diseases can involve the thyroid, kidney, pancreas, neurons, gastric mucosa, adrenals, skin, red cells and synovial membranes as well as thyroglobulin, insulin, deoxyribonucleic acids and immunoglobulins.

For some types of autoimmune and neoplastic diseases, non-specific immunosuppressant treatments, such as whole body X-irradiation or the administration of cytotoxic drugs, have been used with limited success. The disadvantages of such treatment include the toxicity of the agents used, and the increased incidence of various cancers, especially lymphomas and reticulum cell sarcomas, following such therapy. In addition, the use of non-specific agents for chronic cellular suppression greatly increases the susceptibility of the patient to serious infection from environmental fungi, bacteria and viruses which under ordinary circumstances would not cause problems. The invention disclosed herein is specific in that it removes only the pathological effector or those groups of pathological effectors which are related to and responsible for the manifestations of a particular disease.

In viewing the prior art, one finds that most recently there have been generally two approaches to therapeutic treatments for autoimmune and/or neoplastic diseases. The first of these is to introduce a material into the patient which causes a specific type of immunological tolerance to be produced. This suppression of antibody response would then effect a tolerance to the offending antigen. A typical example of this type of approach is U.S. Pat. No. 4,222,907 issued to Katz on Sept. 16, 1981. In this disclosure, the diseased patient is given a therapeutic treatment which consists of introducing conjugates of an antigen linked to a D-glutamic acid: D-lysine copolymer.

The second approach has been the extracorporeal route. The procedures generally involve the removal of whole blood, separation of cellular and soluble blood substances, substitution or treatment of blood plasma and recombination-infusion of the treated whole blood. The first example of this approach would be plasma substitution or exchange with salt, sugar and/or protein solutions and is described by McCullough et al, "Therapeutic Plasma Exchange," Lab. Med. 12(12), p. 745 (1981). Plasma exchange is a rather crude technique that requires a large volume of replacement solution. A second example of this approach involves physical and/or biochemical modification of the plasma portion of whole blood. Typical of the state of the art of this therapeutic treatment are, for example, the Terman et al article "Extracorporeal Immunoadsorption: Initial Experience in Human Systemic Lupus Erythematosus," The Lancet, Oct. 20, 1979, pages 824–826. This article describes a hemodialysis type system utilizing two mechanical filters with a DNA collodian charcoal filter between said two mechanical filters. Typical of this state of the art, however, the adsorbant column is only semispecific for immune components because the charcoal substrate will non-specifically adsorb many vital low molecular weight constituents from the treated plasma. A second application of this approach can be illustrated by the Terman et al article "Specific Removal of Circulated Antigen by Means of Immunoadsorption," FEBS Letters, Vol. 61, No. 1, January, 1976, pages 59–62. This disclosure teaches the specific removal of radiolabeled antigen by antibody treated cellulosic membranes. The author, however, demonstrates that control membranes have a significant capacity to non-specifically adsorb proteins.

A third application of this approach is illustrated by the Bansal et al article "Ex vivo Removal of Serum IgG in a Patient With Colon Carcinoma," Cancer, 42(1), pp. 1–18 (1978). This report teaches the semi-specific adsorption of immunoglobulin by ex vivo treatment of plasma with formalin and heat-killed *Staphylococcus aureas*. The biological activity of certain strains of *S. aureas* is attributed to a molecule present on the cell wall, called Protein A, which interacts and binds with the Fc portion of mammalian IgG. This treatment, because it interacts with the Fc moiety, does not discriminate between normal and pathological IgG components and experiments have shown the possibility of significant side effects.

A fourth application of this approach can be illustrated by the Malchesky et al article "On-line Separation of Macromolecules by Membrane Filtration With Cryogelation," Artif. Organs 4:205, 1980. This publication teaches the semi-specific removal of cryoglobulin substances from plasma by the combination of filtration and cold treatment chambers. The incidence and composition of cryoglobular precipitates are not necessarily consistent with or indicative of many autoimmune or neoplastic diseases.

Another problem associated with the current state of the art is that without systems using mechanical filtration, the specific pathological effectors desired to be removed have not been removed in large enough amounts to do much good for the diseased patient in that the columns do not specifically adsorb substantially only the desired specific pathological effectors.

It has now been found that high specificity of pathological effector removal can be effectuated by treatment of blood and/or plasma in an economical manner using the present invention.

SUMMARY OF THE INVENTION

Broadly stated, this invention relates to a biospecific polymer having immobilized reactive biologicals, wherein the biologicals have a high specific activity for binding complements which are pathological effectors. The biospecific polymer comprises a biocompatible polymer support, with or without a spacer attached to the biocompatible polymer support, which spacer has a physical size that forces it to extend from the surface of the biocompatible polymer support, and a biological or biologicals immobilized on the biocompatible polymer support or optionally on the spacer, via chemical bonding, and characterized in that said biological or biologicals retain their reactivity for binding specific pathological effectors or specific groups of pathological effectors.

This invention also relates to a regimen for the therapeutic treatment of autoimmune diseases comprising passing a diseased patient's blood, plasma or other body fluid over a biospecific polymer having immobilized reactive biologicals, thereby removing the desired pathological effectors from said patient's blood or plasma and then returning said blood to said patient.

This invention also relates to a regimen for harvesting specific components from body fluids by passing a body fluid over a biospecific polymer having an immobilized biological specific for removal of the desired component and desorbing the component from the polymer. The harvested body fluid components, e.g., proteins, hormones, cells, vitamins and immune components may then be utilized for other uses.

Further, this invention, broadly stated, relates to a method of producing these biospecific polymers having immobilized reactive biologicals which have high specific activity for binding complements which are pathological effectors.

Also relating to this invention is a method of producing biospecific polymers on a mechanical support to provide excellent mechanical integrity.

These and other objects of the present invention are disclosed and described in the detailed description below and in the appended claims.

BRIEF DESCRIPTION OF THE DRAWINGS

FIG. 1 represents surface profilometer scans of MEA/HEMA/MMA and GMA/NVP/HEMA terpolymer supports.

DETAILED DESCRIPTION

I. BIOCOMPATIBLE POLYMER SUPPORT

Figure 1A:
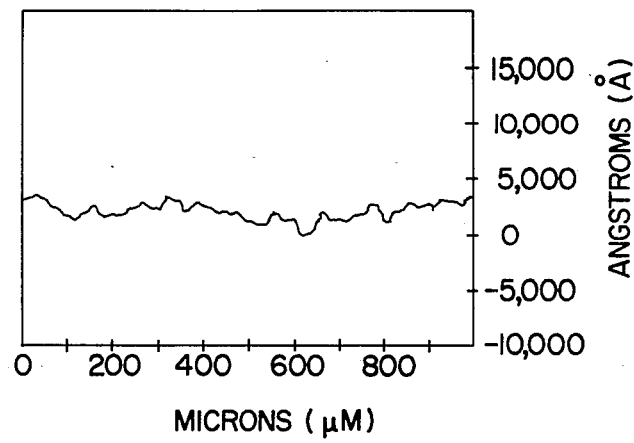
FIG. 1a represents a 1000 micron profilometer scan of a MEA/HEMA/MMA terpolymer support.

The biocompatible polymer supports useful in the present invention are materials which tend not to cause adverse effects when in contact with body fluids such as, for example, plasma or whole blood, while at the same time maintaining a reactive but immobilized biological oriented such that the biological is extended out from the surface of said polymer support. The materials which are suitable are those which may be cast into films and other physical forms, while at the same time being susceptible to having said biologicals chemically bound to them without damaging either themselves or the biologicals bound thereto. The types of materials generally contemplated to be suitable are those known in the art as hydrogels and may be either copolymers or homopolymers.

Modified cellulose and cellulosic derivatives, particularly cellulose acetate, have also found utility as biocompatible supports useful in the present invention. By modified cellulosic derivatives what is meant is that the cellulosic polymer is surface modified by covalently linking pendant biocompatible surface groups to the cellulosic substrate polymer rendering it more biocompatible. Such surface groups are well known and need not be described here, however, for purposes of the present invention, albumin has shown particular utility as a modifying group. Methods of attaching such groups are described hereinbelow.

Homopolymers may also be used as suitable biocompatible polymer supports in the present invention. It is to be understood, however, that when homopolymers are discussed, they include materials which can also be identified as slightly crosslinked homopolymers. That is, they contain a relatively small amount of a second component either intrinsic in the production of the monomer or added purposely to insure enough crosslinking so as to protect the homopolymer from slowly dissolving away in an aqueous media, such as blood. An example of this type of homopolymer which is often slightly crosslinked is hydroxyethyl methacrylate (HEMA).

Referring to the hydrogels, suitable polymers may either be regular homopolymers containing substantially no other material in their matrices, or they may be copolymers prepared from two or more appropriate monomers. In certain instances, this type of tailoring of the copolymers with various monomers may enhance the desirable properties of the biocompatible polymer support material. Examples of suitable monomers which may be copolymerized include hydroxyethyl methacrylate and glycidyl methacrylate.

Also useful are terpolymers which are a subclass of copolymers containing three monomers which are polymerized. An example of suitable terpolymers are glycidyl methacrylate/N-vinyl pyrrolidone/hydroxyethyl methacrylate (GMA/NVP/HEMA) and methyl acrylamidoglycolate methyl ether/hydroxyethyl methacrylate/methyl methacrylate (MEA/HEMA/MMA). Methyl acrylamidoglycolate methyl ether is sold under the trademark MAGME® by American Cyanamid.

In addition to the specific copolymers and homopolymers listed above, copolymers, prepared with or without various additional monomers, and homopolymers suitable in the present invention may be polymerized from the following monomers: alkyl acrylates and alkyl methacrylates; hydroxyalkyl acrylates and hydroxyalkyl methacrylates, for example, hydroxyethyl acrylate, hydroxypropyl acrylate, and hydroxybutyl methacrylate; epoxy acrylates and epoxy methacrylates, such as, for example, glycidyl methacrylate; amino alkyl acrylates and amino alkyl methacrylates and monomers containing active methylene groups, such as, for example, acetoacetoxyethylacrylate and methacrylate; N-vinyl compounds, such as, for example, N-vinyl pyrrolidone, N-vinyl carbazole, N-vinyl acetamide, and N-vinyl succinimide; amino styrenes; polyvinyl alcohols and polyvinyl amines, which must be made from suitable polymeric precursors; acrylamide, methacrylamide; and various substituted acrylamides and methacrylamides; for example, methyl acrylamidoglycolate methyl ether; vinyl pyridine; vinyl sulfonate and polyvinyl sulfate; vinylene carbonate; vinyl acetic acid, and vinyl crotonic acid; allyl amine and allyl alcohol; vinyl glycidyl ether and allyl glycidyl ether. Processes and procedures for creating copolymers and/or homopolymers from the above monomers are well-known and understood in that particular art. These parameters are not critical to the instant invention with the caveat that the final copolymer and/or homopolymer is nontoxic for animal, including human, use.

The method used to cast these materials into a form suitable for use in the present invention is not of critical importance. One presently preferred method is dip coating and is exemplified in Examples 2, 3 and 4.

II. Biologicals

In the context of the present invention, biological and/or biologicals may be defined as a chemical compound which possesses an ability to covalently bond to the biocompatible polymer support or spacer (defined hereinbelow), while at the same time retaining an activity to bind a desired constituent. It is to be understood that, in addition, the biological or biologicals employed must be of such size that they covalently bond to the surface of the polymer support and are not small enough to penetrate the porous matrix of the polymer support and be chemically bonded therefore inside or in the interior of the support material. In this light, a spacer may be employed to insure that the reactive site of the biological, which remains and is susceptible to bonding with the desired pathological constituent, can in fact be presented to this constituent, i.e., that it is held outward away from the support so as to come into contact with the body fluid flowing over the support. It is obvious from the above that, of course, the reactivity for binding the desired pathological constituent is, in fact, retained after immobilization of the biological or biologicals onto the biocompatible polymer support. Examples of materials which may be used as biologicals include: acetylcholine receptor proteins, histocompatibility antigens, ribonucleic acids, basement membrane proteins, immunoglobulin classes and subclasses, myeloma protein receptors, complement components, myelin proteins, and various hormones, vitamins and their receptor components as well as genetically engineered proteins. Particular examples are attaching insulin to a biocompatible polymer support to remove anti-insulin antibody which is associated with the autoimmune disease insulin resistance; attaching anti-Clq and/or Clq and genetically engineered biosynthetic proteins to a biocompatible polymer support to remove immune complexes which are associated with connective tissue and proliferative diseases such as, for example, rheumatoid arthritis and carcinoma.

Referring to genetically engineered proteins, a desired affinity and specificity can be designed into proteinacious biologicals through genetic engineering. By changing the primary structure (e.g., amino acid sequence and/or content) of a proteinacious biological, its active binding site or sites can be modified to decrease its non-specific affinity for essential immune components. With this technology, one can produce biosynthetic proteins which bind avidly to immune complex but only poorly or not at all to essential free immunoglobulin. See, for example, EPO No. 107,509, PCT No. WO84/00774, and U.S. Pat. No. 4,614,513. The former two publications disclose genetic engineering technology directed to the production of Protein A from *S. aureus* and various analogs thereof. The U.S. patent discloses the use of Protein A ligands to remove immunoreactive substances from blood.

To achieve an exclusive specificity for immune complex, a genetically engineered biological having a reduced affinity for immunoglobulin monomer is immobilized in accordance with the present invention so as to promote unhindered binding of the immune complex. In practice, a biospecific polymer having an immobilized genetically engineered biological may be utilized to absorb immune complexes from body fluids while having minimal interference with normal levels of uncomplexed and essential immune components.

Another advantage of genetically engineered biologicals is that a single, specific attachment site can be designed into a protein for use in immobilization onto a biocompatible support. This attachment site can be included in the molecule in such a way so as to minimize the influence of the attachment on the protein thereby preserving biological activity and properly orientating the biological for its intended purpose.

Still another advantage of utilizing a genetically engineered biological is that the molecular weight of the biological can be decreased by eliminating its non-reactive amino acid segments thereby reducing the possibility of immuno-toxicity. It is generally known that high molecular weight molecules ($>$ 10,000 M.W.) may elicit adverse antigenic reactions in body fluids.

Any generally known method of chemical attachment will suffice for immobilizing the biologicals to the biocompatible polymer support, with the caveat that the biological still has at least one active site for the particular autoimmune disease-associated component. Generally, the methods of chemical attachment used fall into three classes or routes of attachment. These three routes are: (1) spontaneous attachment, (2) chemical activation of terminal functional groups, and (3) coupling reagent attachment. Spontaneous covalent attachment of biologicals to polymer support surface proceeds via chemically reactive groups extending from the polymer backbone. Thus, for example, reactive groups such as aldehyde and epoxy extending from the polymer support readily couple biologicals containing available hydroxyl, amino or thiol groups. Also, for example, free aldehyde groups on the polymer support couple via acetal linkages with hydroxyl-containing biologicals and via imide linkages with amino-containing molecules. Additionally, for example, free oxime groups couple via alkylamine, ether and thioether linkages with biologicals containing amine, hydroxyl and thio groups respectively. For purposes of convenience all said attachments and couplings are defined herein as immobilizations. More extensive discussions of these reactions may be found, for example, in "Chemical Procedures for Enzyme Immobilization of Porous Cellulose Beads", Chen, L. F. et al, Biotechnology and Bioengineering, Vol. XIX, pp. 1463-1473 (1977) and "Epoxy Activated Sepharose" 6B, Parmacia Fine Chemicals, Affinity Chromatography, pp. 27-32 (1979).

Chemical activation of terminal functional groups may be accomplished by activating polymer surface functional groups by chemical modification of their terminal components. This method can be exemplified by the oxidation of terminal epoxy functions with periodic acid to form active aldehyde groups. This method is further exemplified in "Immobilization of Amyloglucosidose on Poly [(Glycidyl Methacrylate) Co (Ethylene Dimethacrylate)] Carrier and Its Derivatives", Svec, F. et al, Biotechnology and Bioengineering, Vol. XX, pp. 1319-1328 (1978). The immobilization of the biologicals proceeds as described hereinabove. Condensation reactions may be accomplished between free carboxyl and amine groups via carbodiimide activation of the carboxy groups as is described, for example, in "New Approaches to Non-Thrombogenic Materials", Hoffman et al, *Coagulation—Current Research and Clinical Applications*, Academic Press, N.Y. (1973). Briefly the immobilization of the biologicals is effected by carbodiimide activation by either the polymer or biological carboxyl groups and condensation with a free amine to form a stable peptide bond. The final orientation of the biological is generally a factor as to whether an amine or a carboxyl containing polymer be utilized.

Coupling reagent attachment can be accomplished using a variety of coupling agents to form covalent bridges between polymers and biologicals. Here free hydroxyl and/or amine containing polymers and biologicals are covalently coupled by reagents such as, for example, cyanogen bromide, diisocyanates, dialdehydes and tri-chloro-s-triazine. More exhaustive discussion of this technique may be found for example, in the Chen et al article cited hereinabove.

The preferred method of immobilizing a reactive biological onto a biocompatible polymer substrate in a given case generally is dictated by the molecular locations of the reactive binding moiety of the biological and the functional groups on the biological and polymer substrate which can be covalently combined. For example, it is presently preferred in the case of polymer substrates containing terminal hydroxy or amine functions to activate by treatment with an alkaline solution of cyanogen bromide (10 to 20% w/v). Typically the reaction mixture is maintained at room temperature (20° to 25° C.) for about 30 minutes. The pH of the solution is maintained in a range of about 10 to 12, by the addition of alkaline material, e.g., KOH or NaOH. The polymer is extensively washed with physiological saline (0.9 gm %) and incubated with solutions of a purified biological dissolved in a slightly alkaline buffer solution for 12 to 16 hours at 2° to 8° C. The polymer is extensively rinsed with physiological saline to remove unbound or nonspecifically bound biological components.

Biologicals are immobilized on glycidyl containing polymers via ether, thioether, or alkylamine bonds. Epoxy-activated polymer substrates are rinsed and swollen with aqueous neutral buffer solutions at room temperature. Purified biologicals, dissolved in slightly alkaline (greater than pH 8.0) borate, carbonate or phosphate buffer solutions are incubated with the glycidyl polymer substrate for 12 to 20 hours at 4° to 30° C. Excess and nonspecifically bound biologicals are removed by rinsing the polymer with saline, acetic acid (0.2 to 1.0M) and phosphate-buffered (pH=7.2±0.2) saline solutions. Activation of amine and carboxyl containing polymer matrices is effected by treatment with purified biologicals dissolved in slightly acidic (pH 4.5 to 6.5) buffer solutions of a water soluble carbodiimide. Biologicals are covalently coupled to polymer substrates by incubation of polymer, biological and carbodiimide reactants for 12 to 16 hours at 2° to 8° C. The polymer-biological conjugates are washed alternately in acid then alkaline rinses until the rinse solutions are clear of biological and carbodiimide reactants.

In order to determine the specific binding characteristics of the polymer immobilized biologicals, physiological serum solutions of complementary biomolecules were treated with activated biospecific polymers. The amounts of biomolecule were measured spectrophotometrically and radiochemically. Significant reduction of specific biomolecules resulted following brief exposures to the biologically modified polymer substrates.

III. Spacers

In the present invention, a spacer may be defined as a molecule or compound which is capable of attachment to the surface of a biospecific polymer support, is large enough to extend from the surface of said support and is capable of immobilizing a biological and/or biologicals. The spacer insures that the active site of the biological is held outward away from the support so as to contact the body fluid efficiently. It is obvious from the above that, of course, the reactivity for binding with the desired disease complex is, in fact, retained after immobilization of the biological or biologicals onto the spacer and therefore onto the biocompatible polymer support.

The spacers are derived from organic molecules having at least two reactive functional groups generally situated at opposing ends of the molecule. Such groups serve as attachment vehicles capable of coupling the spacer to the polymer support and to the biological. The reactive functional groups on the spacer may be the same or different with the caveat that they react with functional groups along the surface of the polymer support and the functional groups extending from the biological forming covalent bonds. Any known method for carrying out such coupling reactions will suffice. For example, the methods described hereinabove outlining coupling routes for attaching a biological directly onto a polymer support may be used.

It should also be understood that in cases where a functional group on a spacer is not reactive with functional groups on a biological or on a polymer support, a heterobifunctional crosslinking agent which has the appropriate reactive functional groups to effect a covalent attachment to the biological or to the polymer support may be employed. Examples of heterobifunctional agents useful in the present invention are as follows m-maleimidobenzoyl-N-hydroxysuccinimide ester, succinimidyl-4-(N-maleimidomethyl) cyclohexane-1-carboxylate, succinimidyl 4-(p-maleimidophenyl) butyrate, m-maleimidobenzoyl-N-hydroxysuccinimide ester, sulfo-succinimidyl 4-(N-maleimidomethyl) cyclohexane-1carboxylate, sulfosuccinimidyl-4-(p-maleimidophenyl) butyrate. Compounds with a maleimide moeity on one end and a N-hydroxy succimide ester on the other end, given the proviso that the portion of the compound connecting the two functional groups is non-reactive, may also be employed. Maleimide alternatives, e.g., active halogens and pyridyl disulfides such as N-succinimidyl (4-iodoacetyl) aminobenzoate, sulfosuccinimidyl (4-iodoacetyl) aminobenzoate and N-succinimidyl 3-(2-pyridyldithio) proprionate may also be utilized. Again, compounds with an N-hydroxysuccinimide ester moeity on one end and either an active halogen or a pyridyl disulfide on the other end may be utilized so long as the portion of the compound connecting the two functional groups is non-reactive. As defined herein, a spacer may or may not include heterobifunctional crosslinking agents. It should also be understood that a heterobifunctional crosslinking agent, absent a spacer, may be utilized to effect directly covalent linkages between the polymer support and the biological.

Suitable examples of spacers which may be used in the present invention, where the reactive functional groups are the same, include, for example, $C_2$ to $C_{12}$ diamines, (e.g., 1,6-diaminohexane), divinyl sulfone, glutaraldehyde, 1,4-cyclohexane-dicarboxylic acid, ethylenediamine tetraacetic acid, triethylene glycol, 1,4-butanediol diglycidyl ether and methylene-p-phenyl diisocyanate. Examples of spacers in which the reactive functional groups are not the same include, for example, 6-aminocaproic acid, p-nitrobenzoyl chloride, 1,2-epoxy-3-(p-nitrophenoxy) propane, aminopropyltriethoxy-silane and homocysteine thiolactone.

Polypeptides and proteins may also be used as spacers in the present invention. Albumin, a low affinity protein, for example, has been successfully employed as a spacer. In addition, albumin and other natural proteins serve to render the polymer support more biocompatible.

Finally, it is understood that certain materials may act simultaneously as a spacer and as the activator in the reaction used to combine the spacer and the biocompatible support. Examples of these kinds of compounds, include, for example, gluteraldehyde and 1,4-butanediol diglycidyl ether.

IV. Support Member

Most, if not all, of the suitable biocompatible polymer supports have very low mechanical stability. Most of these materials are, in fact, gels or gel-like as opposed to materials which have high mechanical stability, such as, for example, sheets of polypropylene. Thus, in most embodiments utilizing the present invention, a support member which is mechanically stable is necessary. This support member allows large surface areas to be utilized to insure rapid and medically, as well as commercially, acceptable levels of immune disease-associated component removal. The support member, besides being mechanically stable, should also be inexpensive and must be sterilizable so as to be made compatible for use in a system wherein the blood of a diseased patient is to be treated by the present invention. Examples of materials which are suitable for the present invention as support members include, for example, filter paper, polyester fiber, polycarbonates, reticulated polyurethanes, NORYL ®, a polyphenylene oxide polymer manufactured by the General Electric Company, microporous polymers such as a microporous polypropylene sold under the trademark CELGARD ® by the Celanese Corporation, glass beads and cotton cloth.

Many methods of attaching the biocompatible polymer support having biologicals chemically attached may be utilized. Thus, for example, methods such as spin coating, horizontal casting, vacuum impregnating, dip coating, dip coating with later crosslinking, curtain coating and solution copolymerization may be used. Specific examples of these methods may be found in the examples hereinbelow.

V. Therapeutic Regimen

Broadly stated, the presently contemplated therapeutic regimen of the present invention is for the therapeutic treatment of autoimmune and other diseases comprising exposing a diseased patient's blood or plasma to a biospecific polymer having immobilized reactive biologicals, thereby removing the specific pathological effectors from said patient's blood or plasma and then returning said blood to the patient. This therapeutic treatment may or may not necessitate the use of blood separation techniques. Thus the treatment is contemplated to be carried out in a manner similar to a dialysis treatment with the advantage that total blood separation may not needed and that there is very little if any physical damaging of normal blood components.

It is also possible, of course, to utilize the present invention and the process of the present invention in the treatment of plasma. The plasma may be obtained from whole blood by any of the currently known and practiced methods. Thus, for example plasma may be separated from a patients blood by known methods, then treated by the present invention and the recombined with the other blood components and returned to the patient using currently known procedures. In addition plasma which is being used in known medical treatments may utilize the present invention to treat said plasma before being administered to a patient requiring plasma from a blood bank for example. Obviously whole blood from a blood bank may also be treated by and benefit from the present invention.

It is also to be understood that the current invention may also be used with other "body fluids" to effect removal of pathological effectors.

Because of the advantages of the present invention mentioned above as well as others which will be clear to a person skilled in this art, many types of disease states are contemplated to respond to the present invention used in a therapeutic regimen. Broadly stated six groups of disease states could be advantageously treated. These six disease categories are disorders of immune components, drug excesses, toxin exposure, imbalances of body "substances", infections, and neoplastic states. Many diseases are currently treated using plasmapheresis and cytopheresis where the desired result is removal of a specific substance. The present invention and the process of the invention would apply to these diseases currently treated by plasmapheresis and cytopheresis.

Examples of immune complex diseases which can be treated are, for example, any disease states involving antibody, antigen, antibody-antigen, antigen-antigen and antibody-antibody interactions, cell surface complexes, cytoplasmic complexes, etc.

Examples of drug overdoses which can be treated are, for example, overdoses of iron, digoxin, aspirin, TYLENOL® acetaminophen, methotrexate and other tricyclics.

Examples of poisons and toxins for which the present invention is suitable are, for example, lead, aluminum, mushrooms (Anatoxin) and organic phosphates.

Body "substances" when present in excess can lead to disease. Examples of these which can be eliminated using the present invention include, for example, cholesterol, uric acid, immunoglobulins, sickle cells, uremic toxins, bilirubin, porphyrin, cortisol and prostaglandins.

Some examples of infectious agents which may be treated are, for example, viral disorders such as cytomegalovirus; protozoan disorders such as malaria, trypanosomes and leishmanias; bacterial infections such as strepotococci; fungus infections such as tinea versicolor; mycoplasma such as pleuro-pneumonia-like organisms; rickettsia diseases such as typhus and spotted fevers; spirochetes such as syphilis and chlamydia-agents in the psittacosis lympho-granuloa-trachoma disease group.

Neoplasms which are treatable using the present invention include, for example, the lymphomas, sarcomas, carcinomas and leukemias. These may be removed by specific removal of a cell line, inhibitors, initiators of the disease and combinations thereof.

Further examples of disease states which may be treated using the present invention include, for example, the following:

Infections such as; Post streptococcal glomerulonephritis, Subacute bacterial endocarditis, Secondary syphilis, Pneumococcal sepsis, Lepromatous leprosy, Ventricular shunt infection, Infectious mononucleosis, Typhoid fever, Subacute sclerosing encephalitis, Landry-Guillain-Barre syndrome, Hepatitis B infection, Quartan malaria, Schistosomiasis, and Trypanosomiasis.

Neoplasmas such as; Hepatoma, Lymphoma and Hodgkins disease, Acute leukemia, Hypernephroma, Carcinoma of the colon, Bronchogenic carcinoma, and Burkitts lymphoma.

Connective Tissue Disorders such as; Periarteritis nodosa, Chronic glomerulonephritis, Acute or subacute thyroiditis, Vinyl chloride poisoning, Chronic liver disease, Mixed cryoglobulinemias, Berger's disease or IgA nephropathy, Rapidly progressive glomerulonephritis, and Sickle cell anemia.

Hematologic Diseases such as; Thrombic thrombocytopenic purpura, Autoimmune hemolytic anemia, Idiopathic thrombocytopenic purpura, Idiopathic neutropenia, Cold hemagglutinin disease, Paroxysmal cold hemoglobinuria, Circulating anticoagulants, Acquired hemophilia, the leukemias, the lymphomas, Erythroblastosis fetalis, Pernicious anemia, and Rh diseases.

Neurologic Diseases such as; Acute demyelinating encephalitis, Multiple Sclerosis, Landry's paralysis, Guillain-Barre syndrome, Peripheral neuritis, and Myasthenia gravis.

Collagen Diseases such as; Raynaud's, Lupus Erythematosus, Polyarteritis nodosa, Scleroderma, Dermatomyositis, Sjogren's syndrome, Rheumatoid arthritis, Rheumatic fever, and Erythema nodosa.

Endocrine Diseases such as, for example; Cushing's syndrome & disease, Thyroiditis, Thyrotoxicosis, Addison's disease, and Aspermatogenesis.

Gastrointestinal Diseases such as; Portal cirrhosis, Acute hepatitis, Chronic active hepatitis, Lupoid hepatitis, Biliary cirrhosis, Ulcerative colitis, Regional enteritis, and Pancreatitis.

Miscellaneous Diseases such as, for example; Hypercholesterolemia, Glomerulonephritis, Basement membrane disease, Psychogenic states-drugs, Postaortic valve prosthesis-hemolytic anemia, Exfoliative dermatitis, Id reaction, Psoriasis, Behcet's syndrome, Carcinoma, Subacute bacterial endocarditis, Hypertension, Asthma, Hereditary angioneurotic edema, Meningococcemia, Crohn disease, Hepatic encephalopathy and Raynaud disease.

Further, Diseases characterized by Antibodies to Nuclear Antigens, Cytoplasmic Antigens, Cell Surface Antigens, and Subclasses may be treated by the present invention. Suitable examples include, for example; Antibodies to Native-DNA (double stranded) or single and double stranded, Antibodies to SS DNA, Antibodies to Deoxyribonucleoprotein, Antibodies to Histone, Antibodies to Sm, Antibodies to RNP, Antibodies to Sc 1-1—Scleroderma, Antibodies to SS-A—Sjogren syndrome, Sicca complex, Antibodies to RAP—Rheumatoid Arthritis, Sjogren syndrome, Antibodies to PM-1—Polymyositis-dermatomyositis, and Antibodies to nucleolar—Systemic sclerosis, Sjogren syndrome.

Also, Antibodies Associated With Specific Autoimmune Disorders such as; Antibodies to smooth muscle—Chronic Hepatitis, Antibodies to acetylcholine receptors—Myasthenia gravis, Antibodies to basement membrane at the dermal-epidermal junction—Bullous pemphigoid, Antibodies to the mucopolysaccharide protein complex or intracellular cement substance—Pemphigus, Antibodies to immuno-globulins—Rheumatoid arthritis, Antibodies to glomerular basement membrane—Glomerulonephritis, Goodpasture's syndrome, Idiopathic primary hemasiderosis, Antibodies to erythrocytes—Autoimmune hemolytic anemia, Antibodies to the thyroid—Hashimoto's, Antibodies to intrinsic factor—Pernicious anemia, Antibodies to platelets—Idiopathic thrombocytopenic purpura, Alloimmunization, Antibodies to mitochondria—Primary biliary cirrhosis, Antibodies to salivary duct cells—Sjogren's syndrome, Antibodies to the adrenal—Idiopathic adrenal atropathy, Antibodies to thyroid microsomal—Grave's Disease, Antibodies to thyroglobulin—Addison's Disease, and Antibodies to islet cells—Diabetes Mellitus.

Paraproteinemias such as, for example; Multiple myeloma, Macroglobulinemia, Cryoglobulinemia, and Light chain disease, Hyperlipidemia such as; Primary biliary cirrhosis and Familial Hypercholesterolemia.

Endocrinopathies such as; Grave disease and Diabetes mellitus.

Alloimmunization such as; Hemolytic disease of the newborn and Renal homograft rejection.

Also, suitable for treatment using the present invention include, for example, Post Transfusion Purpura and Autoantibody Diseases such as, Goodpastures syndrome, Myasthenia gravis, Pemphigus vulgaris, Hematological disease, Idiopathic (autoimmune) thrombocytopenic purpura, Autoimmune hemolytic anemia, Inhibitor to factor VIII and Polyradiculopathy/Guillain-Barre Syndrome.

Immune Complex Diseases may also be treated and include, for example; Systemic lupus erythematosus, Polyarteritis nodosa, Cutaneous vasculitis, Rheumatoid arthritis, Glomerulonephritis, and Dermatomyositis.

While not subscribing to any one particular theory over another a review of the probable progression of autoimmune pathology suggests that the pathological sequence is very likely initiated by a free antigen challenge, followed by antibody evolution and complexing and finalized by antibody excess and complement fixation of formed complexes. Thus, for proper selection of the biospecific polymer formulation and provision for proper efficacy would require preliminary diagnostic procedures to determine the predominant form of the autoimmune effector. An illustrative example of this is described below for the treatment of rheumatoid disease. Briefly, rheumatoid disease can be characterized as following the progression from (a) free RF antigen (atypical Ig) (rheumatic condition), (b) free RF antibody evolution and RF complexing and finally (c) antibody excess and complement activated RF complex fixation. Thus treatment of rheumatoid disease in its early development could be determined by detection of atypical immunoglobulins by monoclonal rheumatoid factor (m-RF) antibodies. Treatment at this stage would be best effected by m-RF activated biospecific polymers to remove the offending antigen and thus preventing the evolution of endogenous RF (e-RF) antibodies. Diagnostic evidence of e-RF would indicate the utilization of biospecific polymers having both m-RF and aggregated gamma globulin active biologicals (RF antigen). Alternatively, two biospecific polymers in series, each having one type of active biological could be utilized. In either case this combination of m-RF and aggregated gamma globulin would absorb both the offending antigen and antibody molecules to sequester the disease progression. In the case where significant levels of RF antigen-antibody complex is detected, biospecific polymers containing Clq and/or collagen effector molecules would be indicated. Finally, if the disease process has progressed to the stage of complement fixation of formed immune complexes an effective biospecific polymer would contain one or more anti-complement antibodies such as, for example, anti-Clq, anti-C3 or anti-C4. Again the biologicals, if more than one is desirable, can be immobilized on a single biocompatible support or each can be on a separate support and connected in series in relation to the blood or plasma flow.

As has been proposed above, effective use of the present invention is realized by thorough definition of the dynamics and stage of the immune response for effective disease management.

Today, plasmapheresis and cytophoresis are the treatments for disease by removal of noxious substances or cells from the blood. It is currently believed that any disease treated by plasmapheresis and/or cytopheresis, where the desired result is the removal of a specific substance, can be advantageously treated with the product and process of the present invention.

More specifically, a presently contemplated therapeutic regimen for whole blood may be illustrated as follows:

(a) a vascular access is provided which will allow for;
(b) a blood flow of from about 30 ml/min. to about 200 ml/min.,
(c) an anticoagulant is administered to the blood; and
(d) a pumping means is provided;
(e) the blood is passed in contact with the present invention;
(f) depending on the anticoagulant used, additional medication may be needed or desired to neutralize the anticoagulatory effect on said treated blood;
(g) the treated blood is returned to the patient.

The time frame presently contemplated for the above regimen is approximately from about 2 hours to about 4 hours. It is realized, of course, that depending upon the situation such time frame may be either shortened or lengthened.

A presently contemplated therapeutic regimen for plasma may be illustrated as follows:

(a) a vascular access is provided which will allow for;
(b) a blood flow of from about 30 ml/min. to about 200 ml/min.,
(c) an anticoagulant is administered to the blood; and
(d) a pumping means is provided;
(e) a plasma-formed blood component separation means is provided;
(f) the plasma is passed in contact with the present invention;
(g) filtration through a 0.2 micron filter to remove any microemboli, bacteria and/or fungi;
(h) the treated plasma and the formed blood components are recombined;
(i) depending on the anticoagulant used, additional medication may be needed or desired to neutralize the anticoagulating effect on said treated blood;
(j) the treated blood is returned to the patient.

The vascular access may be provided using well known techniques and procedures in the medical arts. Thus, for example, an indwelling large bore cannula may be used intravenously or arterially. Examples of suitable veins and arteries include the antecubital vein, subclavian vein and brachial or radial arteries. It is further understood that an arterial venous shunt or fistulae (AV shunt) may also be used. In this case the heart is the pumping means. If an AV shunt or fistulae is not used the preferred pumping means during venous access is a roller-peristalic pump capable of providing a flow rate of from about 30 ml/min to about 200 ml/min.

Suitable anticoagulants useful in the process of the present invention include, for example, acid citrate dextrose (approximately 1 ml to every 8 ml of whole blood), heparin, heparin/acid citrate dextrose mixtures (e.g. 1250 IU heparin in 125 ml acid citrate dextrose/L), and prostaglandin. It is to be appreciated that in using anticoagulants such as heparin and prostaglandin it is generally understood that a counteracting medication should be administered to the treated blood or plasma before returning or giving said blood or plasma to a patient.

Further, in the case of treating plasma, it is understood that any conventional methods of removing the formed blood components may be used. Suitable examples of methods of separating plasma from formed blood components include, plasmapheresis, centrifugal cell separation, and cell sedimentation in a plasma bag. Where possible both continuous separation and intermittent (batch) separation are suitable—the aforementioned methods of separation are independent of the present invention and its use.

Finally, the form of the present invention is, generally, not critical. Thus the present invention may utilize a biocompatible support containing the biological in the form of sheets, hollow fibers, cylindrical fibers, reticular networks, cylindrical or rectangular channels, beads and combinations thereof for example. The use of a fluidized bed may also be advantageous in some cases.

EXAMPLE 1

This example describes one method of casting the biocompatible polymer support and a method of chemically attaching a biological directly to the polymer support. This example also is used to describe the use of a system having no mechanical support associated with it.

ABSORPTION OF ANTI-INSULIN ANTIBODIES USING INSULIN ACTIVATED POLY-HYDROXYETHYL METHACRYLATE (p-HEMA):

A. Polymer casting. Solutions of monomer were prepared by combining 15.0 g 2-hydroxyethyl methacrylate (Polysciences Inc., Warrington, PA), 15.0 g ethylene glycol (Fisher Scientific, Pittsburgh, PA), 0.08 g sodium bisulfite (Fisher) and 0.036 g ammonium persulfate (Fisher). The solution was stirred for 15 minutes at room temperature. Approximately 5 ml of solution was placed on a glass plate (5"1 ×5"w× $\frac{3}{8}$"t) in the center of a polyethylene spacer (10 mil thick) cut to form a gasket with a 4"×4" window. A second glass plate was placed over the gasket and solution, clamped in place and the entire assembly incubated at 60° C. overnight. The clamps were removed and the glass plates were pried slightly apart and transferred to a deionized water bath for at least 24 hours. The swollen polymer support was carefully removed from the glass plates and was rinsed-hydrated for at least three days in fresh exchanges of deionized water (500 ml per day).

B. Polymer activation. Discs (5 mm diameter were cut from the polymer sheets for activation and analysis. A 10-20 gm % cyanogen bromide (Eastman Kodak Co., Rochester, NY) solution was prepared by dissolving 1.69 g of finely divided BrCN crystals in 10 ml of 0.2 M $Na_2CO_3$ (pH 11.1) with continuous stirring at 4° C. The pH of the solution was maintained above 11 by the dropwise addition of 5N NaOH until the crystals were dissolved and the pH was stabilized. Four discs were placed in a small sieve and rinsed with approximately 5 ml 0.1N HCl and incubated for 15 minutes in the cyanogen bromide solution. The discs were each rinsed at least two more times with 5 ml portions of 0.1N HCl and incubated overnight in 5.0 ml U-100 regular ILETIN ® insulin injection solution (Eli Lilly, Indianapolis, Ind.) which had been adjusted to a pH of 8.7 by the addition of 1N NaOH. The discs were rinsed with 5 ml 0.5M NaCl, 0.1M $Na_2CO_3$ solution and 3 times in 5 ml aliquots of phosphate (0.05M) buffered saline (0.9 gm %) solution (pH=7.4).

C. Evaluation of biospecific polymer adsorption of anti-insulin antibody. A double antibody competitive binding radioimmunoassay was performed by incubating 560 pg (picogram) $^{125}I$ labeled porcine insulin (New England Nuclear, Boston, MA) and serial dilutions (980 to 15 pg) of non-labeled porcine insulin (Cambridge Nuclear, Billerica, MA) on p-HEMA discs with 280 pg of guinea pig anti-porcine insulin antibody (New England Nuclear) in 0.5 ml of 0.05M phosphate buffered saline (PBS) (pH 7.4) containing 1 gm % bovine serum albumin (BSA) (Sigma Chemical Co., St. Louis, MO) for two hours at room temperature. The p-HEMA discs were removed from each test solution. A 0.1 ml aliquot of goat anti-guinea pig gamma globulin was added to each test tube. The test solutions were mixed and incubated for an additional two hours at room temperature. A 1.0 ml aliquot of cold (2°-4° C.) phosphate buffered saline (pH 7.4) was added to each tube. Each test solution was mixed and centrifuged for 15 minutes at 4° C. at 7500 G and the supernatant decanted into 20 ml scintillation vials. The supernatant was gelled with 5.0 ml Aquasol liquid scintillation fluid (New England Nuclear) and counted in an Isocap 300 Counter (Searle Analytic Inc., Des Plaines, Ill.) for 4.0 minutes. Insulin treated discs adsorbed 111 pg anti-insulin antibody from solution or 283 pg per sq. cm. surface area.

EXAMPLE 2

This example describes how an unsupported biospecific polymer may be produced. It also describes how 6-aminocaproic acid (having a six carbon chain) may be used as a spacer for attaching insulin to the biocompatible polymer support used to remove insulin antibody and adsorption of anti-insulin antibodies using the insulin activated poly-hydroxyethyl methacrylate (p-HEMA) polymer.

A. Polymer casting. Solutions of monomer were prepared by combining 15.0 g 2-hydroxyethyl methacrylate (Polysciences Inc., Warrington, Pa.), 15.0 g ethylene glycol (Fisher Scientific, Pittsburgh, Pa.), 0.08 g sodium bisulfate (Fisher) and 0.036 g ammonium persulfate (Fisher). The solution was stirred for 15 minutes at room temperature. Approximately 5 ml of solution was placed on a glass plate (5" 1×5" w× $\frac{3}{8}$" t) in the center of a polyethylene spacer (10 mil thick) cut to form a gasket with a 4"×4" window. A second glass plate was placed over the gasket and solution, clamped in place and the entire assembly incubated at 60° C. overnight. The clamps were removed and the glass plates were pried slightly apart and transferred to a deionized water bath for at least 24 hours. The swollen polymer was carefully removed from the glass plates and was rinsed-hydrated for at least three days in fresh exchanges of deionized water (500 ml per day).

B. Polymer activation. Polymer discs were prepared as previously described in Example 1. A 10-20 gm % cyanogen bromide (Eastman Kodak Co., Rochester, N.Y.) solution was prepared by dissolving 1.69 g of finely divided BrCN crystals in 10 ml of 0.2 M $Na_2CO_3$ (pH 11.1) with continuous stirring at 4° C. The pH of the solution was maintained above 11 by the dropwise addition of 5 N NaOH until the crystals were dissolved and the pH was stabilized. Four discs were placed in a small sieve and rinsed with approximately 5 ml 0.1 N HCL and incubated for 15 minutes in the cyanogen bromide solution. The discs were each rinsed at least two more times with 5 ml portions of 0.1 N HCl and incubated overnight in 10 ml of a 10 gm % 6-aminocaproic acid solution (w/v) (Sigma Chemical Co.) prepared in 0.1 M $Na_2CO_3$, 0.5 M NaCl buffer solution, pH 8.6. Polymer discs were rinsed with 5 ml 0.1 M $Na_2CO_3$, 0.5 M NaCl buffer and three 5 ml aliquots of phosphate (0.05 M) buffered (pH=7.4) saline (0.9 gm %) solution. The discs were removed from the rinse solution, activated by incubation in 10 ml of a 10% (w/v) 1-cyclohexal-3-(2 morpholinoethyl) carbodiimide (Sigma Chemical Co.) solution prepared in 0.1 M (2[N-morpholino]ethanesulfonic acid) (MES) buffer (pH 6.0) for thirty minutes at room temperature and each disc rinsed in 5 ml of cold (4° C.) phosphate buffered saline solution. Duplicate discs were incubated overnight in 5.0 ml of either U-100 regular ILETIN insulin injection solution or pork insulin regular ILETIN solutions (Eli Lilly, Indianapolis, Ind.) at 4° C. Polymer discs were removed from the protein solutions and rinsed three times in 5 ml of phosphate buffered saline solution.

C. Evaluation of biospecific polymer adsorption of anti-insulin antibody A double antibody competitive binding radioimmunoassay was performed by incubating 560 pg $^{125}$I labeled porcine insulin (New England Nuclear, Boston, Mass.) and serial dilutions (980 to 15 pg) of non-labeled procine insulin (Cambridge Nuclear, Billerica, MA) or p-HEMA polymer discs with 280 pg of guinea pig anti-porcine insulin antibody (New England Nuclear) in 0.5 ml phosphate (0.05 M) buffered (pH 7.4) saline (0.9 gm %) containing 1 gm % bovine serum albumin (Sigma Chemical Co., St. Louis, Mo.) for two hours at room temperature. The p-HEMA discs were removed from each test solution. A 0.1 ml aliquot of goat anti-guinea pig gamma globulin was added to each test tube. The test solutions were mixed and incubated for an additional two hours at room temperature. A 1.0 ml aliquot of cold (2°-4° C.) phosphate buffered saline (pH 7.4) was added to each tube. Each test solution was mixed and centrifuged for 15 minutes at 4° C. at 7500 G and the supernatant decanted into 20 ml scintillation vials. The supernatant was gelled with 5.0 ml Aquasol liquid scintillation fluid (New England Nuclear) and counted in an Isocap 300 Counter (Searle Analytic Inc., Des Plaines, Ill.) for 4.0 minutes. Insulin treated discs adsorbed 271 pg anti-insulin antibody from solution or 690 pg per sq. cm. surface area.

EXAMPLE 3

This example describes a method of casting the biocompatible polymer supports, both with and without mechanical support, via spin casting. This example also describes a second way of chemically binding the biological to the biocompatible polymer support.

ADSORPTION OF ANTI-HUMAN IMMUNOGLOBULIN G(IgG) ANTIBODIES (RHEUMATOID TYPE "FACTORS") USING IMMUNOGLOBULIN ACTIVATED POLY-HYDROXYETHYL METHACRYLATE-CO-GLYCIDYL METHACRYLATE (p HEGL) POLYMERS:

I. Polymer casting. The following example describes the production of both supported and unsupported polymer supports by spin casting techniques.

A. Spin casting device. The spin casting device consists of a closed aluminum drum with ¼ in. thick walls. The inside dimensions of the drum are 4 in. in diameter and 5 in. in length. The drum is connected to a motor (Fisher Dyna-Mix; Fisher Scientific Co., Pittsburgh, Pa.) which spins the drum, and the drum rpm is measured with a strobe phototachometer (Model 1891M Power Instrument Inc., Skokie, Ill.). A heat-blower gun (Fisher Scientific Co.) heats the spinning drum; thermocouples measure the internal drum temperature and the temperature of the air flowing over the drum. The drum is purged with nitrogen before and during the polymerization.

B. Supported polymer production. Whatman Grade 50 hardened filter paper (Fisher Scientific, Pittsburgh, Pa.) was used as a support backing to provide mechanical strength for these spin castings. The paper was cut into rectangular sheets (4-15/16×12-7/16 in.) and then soaked in ethylene glycol (EG) (Fisher Scientific Co., Cat. No. E-177) for 30 min. at room temperature. The excess glycol was drained from the paper; after draining, the paper contained 2-4 g of EG. The conditioned paper was curled in the form of a cylinder and placed inside of the spin casting drum. The outside edge of the paper was pressed against the drum wall to expel any air between the wall and the paper. When the paper is in place, it is preferable but not necessary that the ends of the paper are butted up against each other; there can be some overlap. The paper backing was checked for entrapped air pockets; if any existed, they were removed with a rubber policeman.

For polymerizations which produce a very adhesive polymer, the spin casting cylinder can first be lined with a sheet of silicone release paper by placing the non-treated side of the paper against the cylinder. The conditioned Whatman filter can then be placed against the release paper carefully so as not to entrap air.

C. Polymerization formulations. The following are representative polymerization formulations currently being used. In each case, the initiator was stirred with the reactive monomer(s) at room temperature for 30 minutes or until the initiator dissolved.

| GMA-HEMA (50/50) Copolymer | |
|---|---|
| 6.25 g | 2-Hydroxyethyl Methacrylate (HEMA) |
| 6.25 g | Glycidyl Methacrylate (GMA) |
| 12.5 g | Ethylene Glycol (EG) |
| 0.02 g | 2,2'-Azobis (2-amidinopropane) Hydrochloride (ABAP) |
| GMA-NVP-HEMA (50/40/10) Copolymer | |
| 6.25 g | GMA |
| 1.25 g | NVP |
| 5.00 g | HEMA |
| 12.5 g | EG* |
| 0.02 g | ABAP |

*The ethylene glycol weight includes 2-4 g of EG on the Whatman paper.

D. Spin casting procedure. While the initiator was dissolving in the monomer(s), the drum was loaded into the spin casting assembly. The drum was spun at 1400 rpm at RT and purged with nitrogen for 15 minutes. Then the initiator-monomer solution (25.0 ml) was injected into the drum with a hypodermic syringe having a flexible TEFLON® tip. The nitrogen purge was resumed and the drum speed increased to 2,900 rpm.

The fan (ca. 35 ft$^3$/min.) and heater on the heat gun were started, and the drum was heated at 70°-75° C. for 90 minutes. The heat was then shut off, but the fan was left on to cool the drum until the internal drum temperature dropped to about 30° C. The cool drum was removed from the spin casting apparatus and filled with deionized water. After soaking for an hour, the casting was removed from the drum.

II. Polymer activation. Polymer discs were prepared as previously described in Example 1. Fourteen individual discs were each incubated in 1.0 ml of 1.0 M 1,6-hexane diamine (Eastman Kodak, Rochester, N.Y.) solution for 72 hours at 4° C. The discs were removed from the hexane diamine solution and washed three times with 2 ml phosphate buffered saline solution. A 4.0 gm % human gamma globulin (HGG) (Sigma Chemical Co.) solution was prepared by dissolving 4.0 gm HGG in 100 ml 0.1 M MES buffer (pH 6.0) solution with gentle stirring at room temperature. After the protein was completely dissolved, serial dilutions were made by successive transfers of 1.0 ml protein solution to 9.0 ml MES solution to yield protein concentrations of 4 mg/ml, 400 ug/ml, 40 ug/ml and 4 ug/ml of buffer. Two individual polymer discs were each incubated in 0.5 ml of the protein solutions and 0.5 ml of a 0.25 M 1-ethyl-3-(3-dimethyl-aminopropyl) carbodiimide (Sigma Chemical Co.) solution prepared in MES buffer for 72 hours at 4° C. Each disc was removed from the protein solution and rinsed 3 times with 2 ml of cold (4° C.) phosphate buffered saline.

III. Evaluation of biospecific polymer adsorption of anti-IgG antibody from physiological solutions. A radioimmunoassay was performed by incubating individual discs with 10 ng $^{125}$I goat anti-human IgG (New England Nuclear) in 1.0 ml PBS which contained 1.0 gm % human serum albumin (Sigma Chemical Co.) for two hours at room temperature. The radiotracer solution was removed and each disk was rinsed three times with 2.0 ml PBS solution. The disks were incubated in the last rinse solution overnight at 4° C. Individual disks were removed from the rinse solutions and counted in an Innotron Hydragamma counter (Scientific Products) for one minute each. Counts per minute were converted to disintegrations per minute (DPM) by division with the detector efficiency. The amount of adsorbed antibody was approximated by dividing the average DPM by the radiotracer specific activity. The following results were obtained:

| HGG Treatment (mg/ml) | Anti IgG Adsorbed (pg per sq. cm.)* |
|---|---|
| 20.0 | 2453 |
| 2.0 | 1919 |
| 0.2 | 1271 |
| 0.02 | 664 |
| 0.002 | ** |

*Picograms of radiotracer material per square centimeter of polymer.
**Background activity.

EXAMPLE 4

This example shows the use of amino caproic acid as a spacer for gamma-globulin.

Adsorption of anti-human Immunoglobulin G (Ig G) antibodies (Rheumatoid type "Factors") using immunoglobulin activated poly-hydroxyethyl methacrylate-co-glycidyl methacrylate (p-HEGL) polymers.

A. Polymer casting. Spin Cast p-HEGL polymers were prepared as described in Example 3.

B. Polymer derivatization and activation. Polymer discs were prepared and treated as described in Example 3 except that 1.0 M 6-amino caproic acid (Sigma Chemical Co.) was substituted for hexane diamine as a derivatization and spacer agent.

C. Evaluation of biospecific polymer adsorption of anti-IgG antibody from physioloqical solutions. A radioimmunoassay was performed as described in Example 3 and the following results were obtained:

| HGG Treatment (mg/ml) | anti IgG adsorbed (pg per sq. cm.)* |
|---|---|
| 20.0 | 2395 |
| 2.0 | 1828 |
| 0.2 | 1310 |
| 0.02 | 732 |
| 0.002 | 158 |

*Picograms of radiotracer material per square centimeter of polymer.

EXAMPLE 5

This example shows the use of albumin (67,000 MW) as a spacer for folate. The folate is used to remove folic acid binding protein.

Adsorption of Folic Acid Binding Proteins (FABP) by Folate-Albumin activated poly hydroxyethyl methacrylate (p-HEMA) polymers:

A. Polymer Casting. Filter paper supported p-HEMA polymer sheets were spin cast as described in Example 2 utilizing the following polymer formulation:

| | |
|---|---|
| 15.0 g | 2-Hydroxyethyl Methacrylate |
| 15.0 g | Ethylene Glycol |
| 0.08 g | Sodium Metabisulfite |
| 0.036 g | Ammonium Persulfate |

B. Polymer derivatization and activation. A folic acid Bovine Serum Albumin complex was prepared by carbodiimide condensation of folate carboxyl groups with albumin terminal amine groups. To achieve this 200 mg folic acid (Sigma Chemical Co.) was dissolved in 8 ml 0.1 N NaOH, 400 mg 1-cyclohexyl-3(2-morpholinoethyl)carbodiimide metho-p-toluenesulfonate (Sigma Chemical Co.) was dissolved in 2.0 ml 0.1 M MES buffer (pH 6.0) and 1.0 gm Bovine serum albumin (BSA) was dissolved in 40.0 ml 0.1 M MES buffer. The solutions were combined, mixed and incubated for 72 hours at 4° C. The unreacted folate and carbodiimide was removed from solution by treating 20 ml of the mixture with 20 ml of a BSA (2.5 gm %) - charcoal (1.25 gm %) suspension for thirty minutes at 4° C. The suspension was centrifuged for 15 min. at 3400 G at 4° C. decanted and filtered through a 0.22 micron filter.

Polymer discs were prepared and treated with cyanogen bromide solution as previously described in Example 1. After the discs were rinsed in cold saline solution, sets of eight discs were added to and incubated in 20 ml of either physiological saline, 160 mg % BSA or the folate albumin complex solution previously prepared. The discs were incubated for 72 hours at 4° C. Each disk set was removed from solution, blotted dry and placed in 20 ml saline solution at 4° C. to rinse for at least 24 hours. Duplicate disks were treated with 8 ml of 1% gluteraldehyde solution for 1 minute and rinsed overnight in 20 ml of phosphate buffered saline buffer.

C. Evaluation of biospecific polymer adsorption of folic acid binding protein (FABP) from physiological solution. A competitive protein binding radioassay was performed by incubating 370 pg $^3$H-pteroylglutamic Acid (PGA) (Amersham Corp., Arlington Heights, Ill.) and standard dilutions (48 to 348 pg) of non-radioactive PGA (Sigma Chemical Co.) or p-HEMA polymer discs with 234 pg binding activity of FABP (Kamen, B. A. and Caston, J. D., "Direct Radiochemical Assay for Serum Folate: Competition between $^3$H-Folic Acid and 5-Methyl-tetrahydrofolic Acid for a Folate Binder", J. Lab. Clin. Med., 83, 164, 1974) in 1.0 ml of 0.05 M phosphate buffer (pH 7.6) which contained 20 ul of folate free normal human serum and 5 mg sodium ascorbate (Sigma Chemical Co.). The radioassay tubes were mixed, incubated for 30 minutes at room temperature and 10 minutes at 4° C. Individual discs were removed from the test solutions and 0.5 ml of a cold (4° C.) BSA (2.5 gm %) charcoal (1.25 gm %) suspension was added to each tube. All test solutions were incubated for 10 minutes at 4° C. and centrifuged at 2000 G for 15 minutes at 4° C. The supernatants were decanted into 20 ml scintillation vials. Twelve (12.0) ml liquid scintillation fluid (Fisher Scientific, Pittsburgh, Pa.) was added to each vial. Samples were counted in an Isocap 300

Counter (Searle Analytic Inc.) for 2 minutes each. The following results were obtained:

| Polymer Treatment | FABP Adsorbed (pg/sq. cm.) |
|---|---|
| Saline | 67 |
| Cyanogen Bromide | 54 |
| Bovine Serum Albumin | 39 |
| Folate BSA Complex | 758 |

EXAMPLE 6

A. Polymer preparation. A 30/20/50 (percent by wt.) MEA/HEMA/MMA terpolymer was prepared by combining 129.2 g methyl acrylamidoglycolate methyl ether monomer, 86.4 g 2-hydroxyethyl methacrylate monomer and 216.0 g methyl methacrylate monomer in a MEK/MeOH solvent system in the presence of a polymerization initiator (1.7 g 2,2'-azobis-(2,4-dimethyl valeronitrile dissolved in 20 g MEK). The components were reacted at 60° C. for 24 hrs. giving a terpolymer solution with a 30% solids content.

The terpolymer solution was diluted to a 10% solids content by the addition of solvent (MEK/MeOH) and water. The ratio of MEK to MeOH was consistent to that used in the initial polymerization reaction. The terpolymer solution was coated onto the inside walls of polycarbonate test tubes (Fisher Brand 11×75 mm) by filling each tube with the terpolymer solution then decanting the solution from the tubes. The terpolymer coated tubes were inverted (open end down) and placed in a rack to air dry overnight, giving a thin, cured, adherent film.

B. Biological immobilization. A 0.1 gm % solution of chemically aggregated human immunoglobin (AgIg) in 50/50 MES/borate buffer (pH 9) was prepared. One ml of this solution was added to each polymer coated tube and allowed to react with the polymer for 4 hrs. at room temperature. The AgIg solution was decanted from the tubes. Each tube was rinsed 3 times with deionized water and then subjected to 2 successive 15 min. soakings in a detergent wash solution (0.05% TWEEN-20/saline) and rinsed 3 more times with deionized water to remove any unbound AgIg. Tubes bearing the immobilized biological were stored in PBS containing sodium azide as a preservative until they were bioassayed.

To determine the amount of AgIg immobilized onto the surface of the polymer, a duplicate set of polymer coated tubes was prepared as above except that radiolabeled human aggregated immunoglobulin $^{125}$I AgIg was employed as the biological. The polymer coated tubes with immobilized $^{125}$I AgIg were counted in an Innotran Hydragamma radiation counter (Scientific Products). The detected counts per min (CPM) were converted to DPM by division with the detector efficiency. The amount of immobilized AgIg was calculated by dividing the average DPM from replicate tubes by the radiotracer specific activity. The results are presented in Table 1.

C. Evaluation of biospecific polymer adsorption.

Radioimmunoassay: A radioimmunoassay was performed to determine the activity of the biospecific polymer. 3 ml of 1 gm % BSA blocking agent was added to each polymer coated tube with immobilized AgIg. The tubes were covered and stored overnight at 4° C. The blocking agent was decanted from the tubes and 1.0 ml of mouse monoclonal antihuman aggregated immunoglobulin G (anti-AgIg) dissolved in PBS containing 1% BSA was added to each tube. The tubes were covered and incubated at 37° C. for 2 hrs. The anti-AgIg solution was decanted from the tubes. The polymer in each tube was washed 3 times (10 min. soakings) with a 0.05% TWEEN-20/saline detergent solution. The polymer in each tube was washed one more time with the TWEEN-20 solution which was immediately decanted from the tube. Goat anti-mouse immunoglobulin (anti-mouse Ig) dissolved in 1 gm % BSP in PBS and tagged with $^{125}$I was added to each tube and incubated at 37° C. for 3 hrs. The radiolabeled anti-mouse Ig solution was aspirated from each tube. The polymer was then washed in the TWEEN-20/saline detergent solution as described above. Each polymer coated tube was counted in a radiation counter as before. The amount of anti-mouse Ig adsorbed was calculated by converting CPM to DPM and dividing the average DPM from replicate tubes by the specific activity of the tracer solution. Results are presented in Table 1.

Colormetric assay: An ELISA colormetric assay was performed as an alternate method to determine the activity of the biospecific polymer. 3.5 ml of 1 gm % BSA blocking agent in PBS was added to each polymer coated tube with immobilized AgIg and to control tubes without immobilized biologicals. The tubes were incubated for 1 hr. at room temperature and the BSA solution was decanted from the tubes. HRP-labeled mouse monoclonal antihuman AgIg (HRP-monoclonal antibody) in PBS containing 1% BSA was carefully added to each tube and incubated for 2 hrs. at room temperature. The HRP-monoclonal antibody solution was aspirated from each tube. Each tube was washed 3 times (10 min. soakings) with 0.05% TWEEN-20/saline detergent solution. After each washing the detergent solution was aspirated from each tube. Following the third wash, each tube was again filled with the TWEEN-20/saline detergent solution. The solution was immediately decanted from the tubes and the tubes were rinsed with deionized water. At Time Zero 3.0 ml of ABTS/hydrogen peroxide color reagent (Kirkegaard & Perry Laboratories, Inc., Gaithersburg, Md.) was added to each tube at 15 sec. intervals. One-half hour following the addition of the color reagent, each tube was shaken on a VORTEX-GENIE ® mixer. The contents of each tube were then emptied into a cuvet for spectrophotometric analysis. The samples were analyzed at 414 nm on a UV-VIS Spectrophotometer (Hewlett Packard Model 8450). The results are presented in Table 1.

D. Comparative testing. For comparative purposes, a 50/46/4 percent by wt GMA/NVP/HEMA (Standard) polymer solution with 10% solids content was prepared and coated onto the inside walls of polycarbonate test tubes as previously described. After air drying, the polymer was derivatized with ACA (amino caproic acid) by placing 3 ml of 0.25M 6-amino caproic acid in each polymer coated tube and reacting for 3 hrs. at room temperature. The ACA solution was decanted from each tube and the polymer was rinsed 3 times with deionized water. The tubes were filled with 1N HCl to hydrolyze any unreacted epoxy groups on the ACA derivatized polymer. After 1 hr. the acid was decanted off and the polymers were rinsed 3 times with deionized water. The tubes were then filled with PBS containing sodium azide and stored overnight at room temperature. The PBS solution was decanted from the tubes and the polymer with pendent ACA spacer arms were rinsed 3 times with deionized water. The ACA pendent spacer arms were activated by the addition of 3 ml of 0.1M EDC in 0.05M MES buffer (pH 5.5) to each tube for one-half hour. The EDC solution was decanted off and the polymers were rinsed 3 times with deionized water. 3 ml of 1 gm % AgIg in 50/50 MES/borate buffer (pH 9) was added to each tube and reacted for 4 hrs. at room temperature. The biospecific polymers were washed and rinsed as before with detergent solution. A duplicate set of polymer coated tubes was similarly prepared except the radiolabeled ($^{125}$I) AgIG was employed. Reagent volumes for both the MEA/HEMA/MMA and GMA/NVP/HEMA terpolymers were 1 ml/tube for protein immobilizations and radioactive assays and 3 ml/tube for the ELISA colormetric assay.

The GMA/NVP/HEMA polymer was evaluated for protein immobilization, and polymer adsorption as described in sections B and C above. Results are presented in Table 1.

| Solids Content (% by wt) | Water Content (% by wt) | Surface Appearance | Pore Size (um) |
|---|---|---|---|
| 10 | 0 | smooth | — |
| 10 | 2 | smooth | — |
| 15 | 8 | low porosity | 0.2–2.0 |
| 10 | 8 | intermediate porosity | 0.2–2.0 |
| 5 | 15 | high porosity | 0.3–3.0 |

EXAMPLE 8

This example illustrates the preparation and efficacy of a biospecific polymer having an immobilized genetically engineered biological for binding human IgG, aggregate (aggregated IgG is the standard model employed in studying immune complex diseases).

A. Polymer preparation. A 30/20/50 MEA/HEMA/MMA polymer solution having a 10 percent

TABLE 1

| CHEMISTRY | PROTEIN LOADING | | | BIOACTIVITY RADIOACTIVE ASSAY | | |
|---|---|---|---|---|---|---|
| | DPMS Bound[1] | ug AgIg per Tube[2] | ug AgIg per cm[2] | Chemistry and Biological Immobilized | DPMS Bound[3] | Corrected DPMS Bound[4] |
| GMA/NVP/HEMA (STANDARD) | 567 | 5.5 | 0.92 | GMA/NVP/HEMA (STANDARD) AgIg BSA Control AgIg Control | 10251 268 1624 | 8627 |
| MEA/HEMA/MMA (2% H$_2$O) | 300 | 2.9 | 0.49 | MEA/HEMA/MMA (2% H$_2$O) AgIg BSA Control AgIg | 11314 248 1707 | 9607 |
| MEA/HEMA/MMA (5% H$_2$O) | 286 | 2.8 | 0.47 | MEA/HEMA/MMA (5% H$_2$O) AgIg BSA Control AgIg Control | 12043 212 1644 | 10399 |

| BIOACTIVITY | | | | |
|---|---|---|---|---|
| RADIOACTIVE ASSAY | | COLOR ASSAY | | |
| ug Anti-Mouse Ig (AB$_2$) | Activity As a % of Standard | Absorbance | Corrected Absorbance[5] | Activity As a % of Standard |
| 0.87 | — | 0.2514 0.0097 | 0.2417 | — |
| 0.96 | 110 | 0.6635 0.0108 | 0.6527 | 270 |
| 1.0 | 115 | 0.7286 0.0060 | 0.7226 | 299 |

[1]Specific activity of the radioactive protein solution is 104 DPM/ug.
[2]Surface area evaluated is 5.9 cm$^2$.
[3]Specific Activity of the radioactive antibody (AB$^2$) solution is 9956 DPM/ug.
[4]Figures corrected for background binding of the second antibody to the immobilized AgIg (AgIg Control:. BSA Control figures are negligible.
[5]Figures corrected for background absorbance on BSA control tubes.

EXAMPLE 7

To determine the effect of varying the water and solids content in the 30/20/50 MEA/HEMA/MMA polymer formulations on the surface characteristics of the polymer after curing, samples of the polymer were examined by scanning electron microscopy (SEM). The polymer formulations were prepared as described in Example 6 except a 75/25 (by wt.) MEK to methanol solvent ratio was employed. The water and solids content was varied as indicated below. 2×3 inch polycarbonate strips were dip coated with each polymer formulation and air cured overnight. Cured samples were then examined by SEM at 6000 magnification for surface porosity.

solids and 2 percent water content was prepared as in Example 6. 300 ul of the terpolymer solution was pipetted into microtiter wells (375 ul vol. Dynatech Labs. The wells were shaken to disperse the terpolymer solution over the inside walls of the wells. Excess terpolymer was decanted from the wells. The terpolymer wells were inverted (open end down) and allowed to air dry for 16 hrs. at room temperature giving a cured adherent film. The terpolymer in each well was hydrated by submerging the wells in deionized water for 2 hrs., (after which the water was changed and the wells were submerged for an additional 2 hrs.).

B. Diamine derivation of polymer. 200 ul of 25 mM of putrescine dihydrochloride in 0.2 M sodium phosphate buffer (pH 12.0) was added to each polymer coated well and incubated for 2 hrs. at room temperature. The putrescine solution was decanted and the polymers were washed 4 times by filling each well with deionized water and suctioning the well dry.

C. Attachment of S-MBS heterobifunctional crosslinker. 100 ul of 5 mM Maleimidobenzoylsulphosuccinimide ester (S-MBS) in PBS (pH 7.2) was placed in each well and reacted with the putrescine derivatized terpolymer for 1 hr. at room temperature. The S-MBS solution was then suctioned off and the S-MBS activated putrescine terpolymer was rinsed 3 times as before with deionized water.

D. Attachment of biological. Three different genetically engineered protein A binding fragments (FB-32, 36 and 37 obtained from Creative Biomolecules, Inc., Hopkinton, Mass.) were immobilized on 3 sets of polymer coated wells as set forth below. 100 ul of the genetically engineered protein A binding fragment dissolved in PBS (200 ug/ml) was placed in each polymer coated well and incubated for 2 hrs. at room temperature. The binding fragment solution was then aspirated from each well and the wells were washed 4 times with 0.02% TWEEN-20/saline detergent solution allowing a 5-minute incubation period with the detergent solution between each wash.

E. Evaluation of biospecific polymer adsorption of immune complex. Competitive binding assays were conducted on each of the 3 sets of polymer coated wells with monomeric IgG and aggregated IgG to determine the specificity of the biospecific polymers for immune complex. Aggregated IgG is the classic model for studying immune complex diseases.

The biospecific polymers in the wells were incubated for 1 hr. in blocking solution (1 percent BSA in PBS) to eliminate non-specific binding. The blocking solution was decanted from the wells and 100 ul of varying concentrations (see Table 2) of unlabeled and $^{125}$I labeled monomeric IgG (Ig) and heat aggregated IgG (AgIg) in blocking solution were added alone and in combination to each polymer coated well and incubated with gentle agitation for 2 hrs. at room temperature. The polymers were then washed 6 times in 0.02% TWEEN-20/saline PBS with a 5 min. incubation between washes. The wells were broken apart and put into 13 ×100 mm test tubes and counted on a gamma counter. CPM was converted to DPM by division with the detector efficiency. The amount of monomer or aggregate bound was calculated by dividing the average DPM from replicate tubes by the radiotracer specific activity.

TABLE 2

Concentration of Ig and AgIg Employed
1000 ug/ml $^{125}$I AgIg
200 ug/ml $^{125}$I Ig
1300 ug/ml Ig
1000 ug/ml $^{125}$I AgIg + 1300 ug/ml Ig
200 ug/ml $^{125}$I AgIg + 1300 ug/ml Ig
1300 ug/ml $^{125}$I Ig + 1000 ug/ml AgIg
1300 ug/ml $^{125}$I Ig + 200 ug/ml AgIg Amount of $^{125}$I Labeled Material Bound (ug)

|  |  | $^{125}$I AgIg | $^{125}$I Ig | $^{125}$I AgIg + Ig | $^{125}$Ig + AgIg | $^{125}$I AgIg + Ig $^{125}$I Ig + AgIg |
|---|---|---|---|---|---|---|
| FB-32 | Ig (1300 ug/ml) | — | 0.2 | — | — | — |
|  | AgIg (1000 ug/ml) | 7.4 | — | 2.9 | 0.3 | 9.7 |
|  | AgIg (200 ug/ml) | 1.7 | — | 0.9 | 0.1 | 9.0 |
| FB-36 | Ig (1300 ug/ml) | — | 0.5 | — | — | — |
|  | AgIg (1000 ug/ml) | 4.5 | — | 4.0 | 0.3 | 13.3 |
|  | AgIg (200 ug/ml) | 1.7 | — | 1.6 | 0.2 | 8.0 |
| FB-47 | Ig (1300 ug/ml) | — | 0.5 | — | — | — |
|  | AgIg (1000 ug/ml) | 11.5 | — | 11.5 | 0.8 | 14.4 |
|  | AgIg (200 ug/ml) | 3.0 | — | 2.5 | 0.5 | 5.0 |

EXAMPLE 9

Polymer coated wells were prepared and derivatized as previously set forth in Example 8. Genetically engineered protein A binding fragments (FB-32 and 47 Creative Biomolecules, Inc.) were each immobilized on 2 different sets of polymer coated wells. Competitive binding assays were conducted on each set of biospecific polymer to determine its specificity for immune complex. The assay procedure and concentration of AgIg were the same as set forth in Example 8 except that the concentration of monomeric Ig was increased ten-fold to 13,000 ug/ml. The assay results are given below.

| | | Amount of $^{125}$I Labeled Material Bound (ug) | | | | |
|---|---|---|---|---|---|---|
|  |  | $^{125}$I AgIg | $^{125}$I Ig | $^{125}$I AgIg + Ig | $^{125}$Ig + AgIg | $^{125}$I AgIg + Ig $^{125}$I Ig + AgIg |
| FB-32 | Ig (13,000 ug/ml) | — | 4.3 | — | — | — |
|  | AgIg (1000 ug/ml) | 4.7 | — | 4.5 | 3.7 | 1.2 |
|  | AgIg (200 ug/ml) | 1.2 | — | 0.8 | 2.7 | 0.3 |
| FB-47 | Ig (13,000 ug/ml) | — | 5.3 | — | — | — |
|  | AgIg (1000 ug/ml) | 5.4 | — | 6.2 | 4.7 | 1.3 |
|  | AgIg (200 ug/ml) | 2.7 | — | 1.7 | 5.8 | 0.3 |

EXAMPLE 10

Figure 1B:
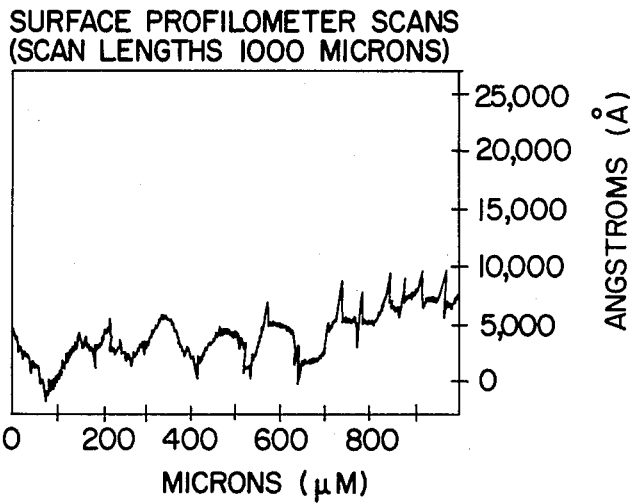
FIG. 1b represents a 1000 micron profilometer scan of a GMA/NVP/HEMA terpolymer support.
Figure 1C:
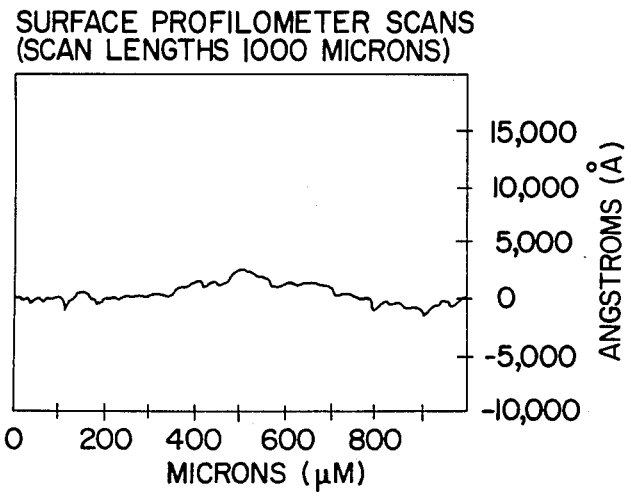
FIG. 1c represents a 1000 micron profilometer scan of a polycarbonate support.

To compare the relative surface roughness of the MEA/HEMA/MMA and GMA/NVP/HEMA terpolymer supports, surface profilometer scans (DEKTAK II surface profilometer, Sloan Technology, Corporation, Santa Barbara, Calif.) were taken of each polymer surface. The polymer formulations were prepared as described in Example 6. The solids content of the polymer formulations was 10 percent. The water content of the MEA/HEMA/MMA and GMA/NVP- /HEMA were 2 and 15 percent, respectively. Polycarbonate strips were dip coated with the respective polymer formulations and air cured overnight. The scan results are shown in FIG. 1 and indicate that the MEA/HEMA/MMA terpolymer surface is less irregular than the GMA/NVP/HEMA standard.

EXAMPLE 11

This example illustrates the relative cell adhesion characteristics of MEA/HEMA/MMA and GMA/NVP/HEMA terpolymer supports for non-specific cell adhesion.

Figure 2:
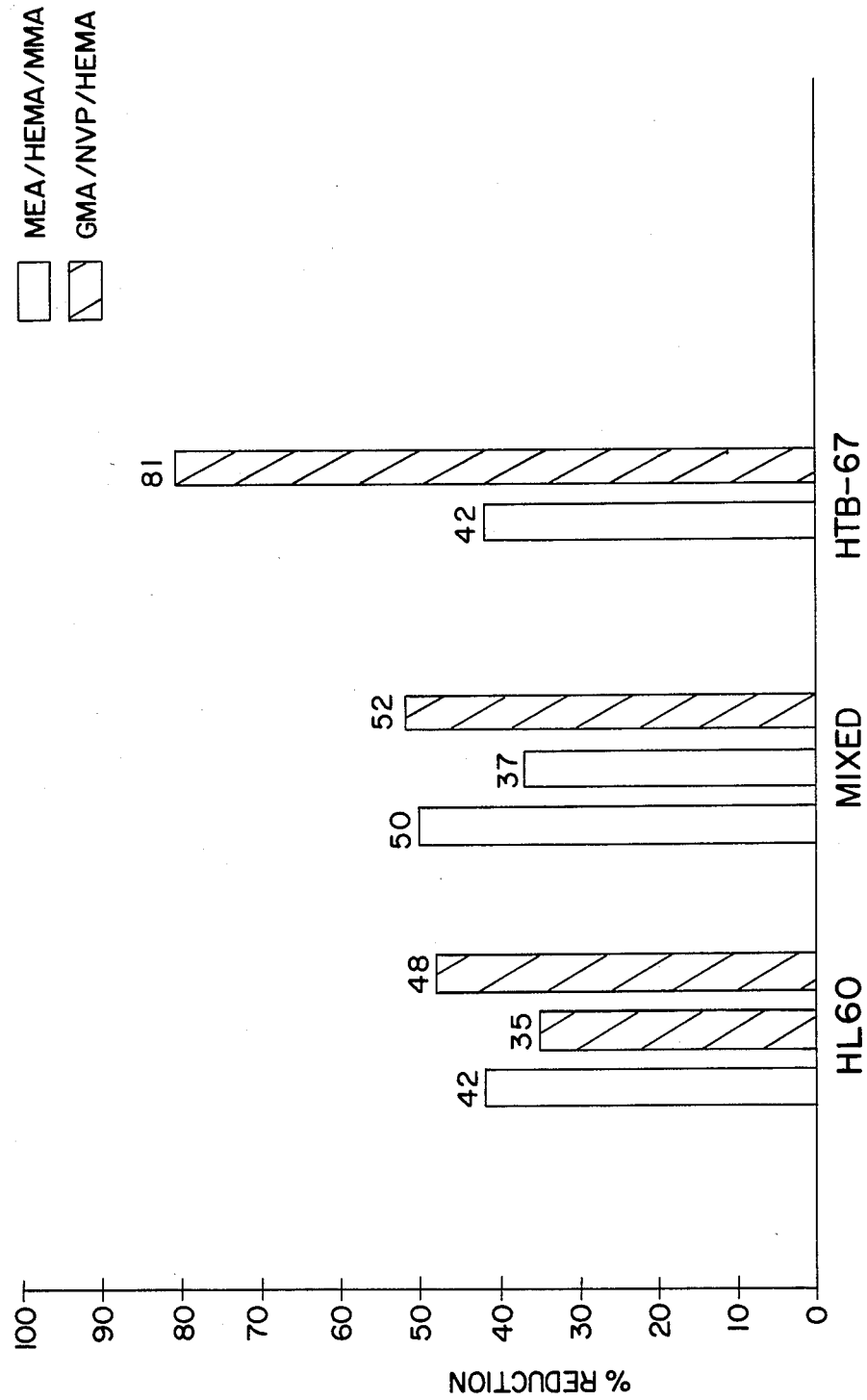
FIG. 2 represents a histogram comparing the relative cell adhesion characteristics of MEA/HEMA/MMA and GMA/NVP/HEMA terpolymer supports.

Two polymer formulations, standard 50-46-4 GMA-NVP-HEMA and 30-20-50 MAGME-HEMA-MMA, were prepared as in Example 6. The cured polymer supports (without biologicals) were compared for cellular adsorption with homogeneous and mixed cancer cell lines (HL60-leukemia and HTB67-melanoma). Cellular suspensions were recirculated past the hydrolyzed terpolymer supports, periodically sampled and quantitated in a COULTER ® cell counter (Coulter Electronics Ltd.). The amount of cells remaining in the recirculation media subtracted from the initial cell amount before circulation, is an indication of the number of cells non-specifically adsorbed onto the terpolymer support. The results, illustrated in FIG. 2, show that the MEA/-HEMA/MMA polymer has superior non-specific adsorption characteristics when individual cell lines are examined.

The above-described examples serve to illustrate the present invention without restricting it in any way. It will be obvious to those in the art that various changes and modifications may be made without departing from the spirit and scope of the present invention.

What is claimed is:

1. A biospecific polymer comprising:
   (a) a biocompatible terpolymer support comprising methyl acrylamidoglycolate methyl ether, hydroxyethyl methacrylate and methyl methacrylate; and
   (b) a biological or biologicals immobilized on said terpolymer support via chemical bonding and wherein said biological or biologicals retain their reactivity for adsorbing specific pathological effectors or specific groups of pathological effectors.

2. A biospecific polymer comprising:
   (a) a biocompatible terpolymer support comprising methyl acrylamidoglycolate methyl ether, hydroxyethyl methacrylate and methyl methacrylate;
   (b) a spacer bonded to said biocompatible terpolymer support; and
   (c) a biological or biologicals immobilized on said spacer via chemical bonding and wherein said biological or biologicals retain their reactivity for adsorbing specific pathological effectors or specific groups of pathological effectors.

3. A biospecific polymer as claimed in claims 1 or 2 further characterized in that said terpolymer support is fixed to a mechanically stable support member.

4. A biospecific polymer as claimed in claim 3 wherein said mechanically stable support member is selected from the group consisting of polyester fiber, microporous polyolefins, cotton cloth, polystyrene, polycarbonate, polyphenylene oxide, glass beads, reticulated polyurethanes and combinations thereof.

5. A biospecific polymer as claimed in claims 1 or 2 wherein said biologicals are selected from the group consisting of acetylcholine receptor proteins, histocompatibility antigens, ribonucleic acids, basement membrane proteins, genetically engineered proteins, immunoglobulin classes and subclasses, myeloma protein receptors, insulin complement components, myelin proteins, hormones and their receptor components, vitamins and their receptor components or combinations thereof.

6. A biospecific polymer comprising:
   (a) a biocompatible terpolymer support comprising methyl acrylamidoglycolate methyl ether, hydroxyethyl methacrylate and methyl methacrylate; and
   (b) a biological or biologicals immobilized on said terpolymer support via chemical bonding and wherein said biological or biologicals retain their reactivity for adsorbing specific body fluid components.

7. A biospecific polymer comprising:
   (a) a biocompatible terpolymer support comprising methyl acrylamidoglycolate methyl ether, hydroxyethyl methacrylate and methyl methacrylate;
   (b) a spacer bonded to said biocompatible terpolymer support; and
   (c) a biological or biologicals immobilized on said spacer via chemical bonding and wherein said biological or biologicals retain their reactivity for adsorbing specific body fluid components.

8. A biospecific polymer as claimed in claims 1 or 2 wherein said biological is a genetically engineered biosynthetic protein used to remove immune components which are associated with immune complex diseases.

9. A biospecific polymer as claimed in claim 2 wherein said spacer is selected from the group consisting of $C_2$ to $C_{12}$ diamines, glutaraldehyde, 1,4-cyclohexanedicarboxylic acid, ethylenediamine tetraacetic acid, triethylene glycol, 1,4-butanediol diglycidyl ether, methylene-p-phenyl diisocyanate, 6-aminocaproic acid, p-nitrobenzoyl chloride, 1,2-epoxy-3-(p-nitrophenoxy) propane, aminopropyltriethoxy-silane, succinic anhydride, homoapteine thiolactone and albumin and combinations thereof.

10. A therapeutic treatment of diseases which comprises passing a diseased patient's body fluid in contact with a biospecific polymer comprising a biocompatible terpolymer support comprising methyl acrylamidoglycolate methyl ether, hydroxyethyl methacrylate and methyl methacrylate having immobilized reactive biologicals where said biologicals adsorb specific pathological effectors or groups of pathological effectors associated with said patient's disease state and returning said body fluid to said patient.

11. A therapeutic treatment of diseases which comprises passing a diseased patient's body fluid in contact with a biospecific polymer comprising a biocompatible terpolymer support comprising methyl acrylamidoglycolate methyl ether, hydroxyethyl methacrylate and methyl methacrylate, a spacer attached to said biocompatible terpolymer support and a biological immobilized on said spacer wherein said biologicals adsorb specific pathological effectors or specific groups of pathological effectors associated with said patient's disease state and returning said body fluid to said patient.

12. A therapeutic treatment of diseases which comprises passing a body fluid which is to be administered to a patient, prior to said body fluid being administered to said patient, in contact with a biospecific polymer comprising a biocompatible terpolymer support comprising methyl acrylamidoglycolate methyl ether, hydroxyethyl methacrylate and methyl methacrylate, having immobilized reactive biologicals, thereby adsorbing and removing specific pathological effectors from said body fluid, and then introducing said body fluid to said patient.

13. A therapeutic treatment of diseases which comprises passing a body fluid which is to be administered to a patient, prior to said body fluid being administered to said patient, in contact with a biospecific polymer comprising a biocompatible terpolymer support comprising methyl acrylamidoglycolate methyl ether, hydroxyethyl methacrylate and methyl methacrylate, a spacer attached to said biocompatible terpolymer support and a biological immobilized on said spacer, thereby removing specific pathological effectors from said body fluid, and then introducing said body fluid to said patient.

14. A therapeutic treatment as claimed in claims 10, 11, 12 or 13 wherein two or more biospecific polymers each having the same or different reactive biologicals or groups of biologicals immobilized thereon are utilized in series to remove said specific pathological effectors.

15. The therapeutic method as recited in claims 10, 11, 12 or 13 wherein the body fluid to be treated is selected from the group consisting of blood, whole blood, blood plasma, and cerebrospinal fluid.

16. A method of harvesting components from body fluids which comprises passing a body fluid in contact with a biospecific polymer comprising methyl acrylamidoglycolate methyl ether, hydroxyethyl methacrylate and methyl methacrylate, and having immobilized thereon reactive biologicals specific for the desired body fluid component to be harvested, thereby adsorbing the desired component from said body fluid.

* * * * *